(12) United States Patent
Waldrop, III et al.

(10) Patent No.: US 7,718,576 B2
(45) Date of Patent: May 18, 2010

(54) PEROXIDE-BASED CHEMILUMINESCENT ASSAYS AND CHEMILUMINESCENT COMPOUNDS USED THEREIN

(76) Inventors: Alexander A. Waldrop, III, 260 Westbrook St. #10, South Portland, ME (US) 04106; Calvin P. H. Vary, 81 Nash Rd., Windham, ME (US) 04062

( * ) Notice: Subject to any disclaimer, the term of this patent is extended or adjusted under 35 U.S.C. 154(b) by 788 days.

(21) Appl. No.: 10/457,385

(22) Filed: Jun. 10, 2003

(65) Prior Publication Data
US 2003/0219844 A1 Nov. 27, 2003

Related U.S. Application Data

(62) Division of application No. 09/463,990, filed as application No. PCT/US98/17294 on Aug. 21, 1998, now abandoned.

(60) Provisional application No. 60/056,518, filed on Aug. 21, 1997.

(51) Int. Cl.
*C40B 30/00* (2006.01)
(52) U.S. Cl. .......................... 506/7; 546/104
(58) Field of Classification Search .............. None
See application file for complete search history.

(56) References Cited

U.S. PATENT DOCUMENTS

| | | | |
|---|---|---|---|
| 3,352,791 A | | 11/1967 | Sheehan |
| 4,410,633 A | * | 10/1983 | Hertl et al. .................. 435/7.1 |
| 4,486,530 A | * | 12/1984 | David et al. ................ 435/7.91 |
| 4,933,276 A | * | 6/1990 | Baret ......................... 435/7.92 |
| 5,284,951 A | | 2/1994 | McCapra et al. |
| 5,321,136 A | * | 6/1994 | McCapra .................... 546/104 |
| 5,338,847 A | | 8/1994 | McCapra |
| 5,565,570 A | | 10/1996 | Mattingly et al. |
| 5,594,112 A | | 1/1997 | Sato et al. |
| 5,783,696 A | | 7/1998 | Kinkel et al. |

FOREIGN PATENT DOCUMENTS

| | | |
|---|---|---|
| EP | 0212 951 | 4/1987 |
| GB | 2112779 | 6/1983 |
| WO | WO92/09580 | 6/1992 |
| WO | WO 96/37456 | * 11/1996 |

OTHER PUBLICATIONS

White et al., J. Am. Chem. Soc. 109:5189-5196 (1987).*
Rapaport, E. et al.: J. Amer. Chem. Soc. May 3 1972, vol. 94, No. 9, pp. 3153-3159.
Rauhut, M.M et al.: J. Orgainc Chem., Nov. 1965, vol. 30, pp. 3587-3592.
J. Orgainc Chem., Nov. 1965, vol. 30, pp. 3587-3592.

* cited by examiner

*Primary Examiner*—Jeffrey S. Lundgren

(57) ABSTRACT

A compound is provided having the formula:

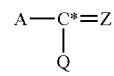

where C* is an sp² coordinated carbon atom;
A is defined by the formula

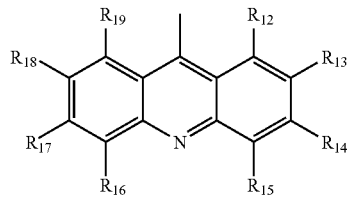

wherein $R_{12}$, $R_{13}$, $R_{14}$, $R_{15}$, $R_{16}$, $R_{17}$, $R_{18}$ and $R_{19}$ are independently selected from the group consisting of hydrogen, alkyl, alkoxy, aryl, alkylaryl, heteroaryl, heteroalkoxy, aldehyde, keto, amino, nitro, halo, sulfate, sulfonyl, carboxy, carboxyester, phosphate or phosphoester, each of which may be substituted or unsubstituted;
Z is a moiety that is covalently bonded to C* selected from the group consisting of O, S, N—$R_1$, and +N—$R_1R_2$ where $R_1$ and $R_2$ are selected from hydrogen, alkyl, alkoxy, aryl, alkylaryl, heteroaryl, or heteroalkoxy moieties, each of which may be substituted or unsubstituted; and
Q is a suitable leaving group yields a compound which is capable of exhibiting a chemiluminescent reaction in the presence of a peroxide or peroxide-like compound under aqueous or mixed aqueous-organic conditions.

20 Claims, 10 Drawing Sheets

PEROXIDE-BASED CHEMILUMINESCENT ASSAYS AND CHEMILUMINESCENT COMPOUNDS USED THEREIN

This application is a divisional of application Ser. No. 09/463,990, filed on Feb. 18, 2000 now abandoned and for which priority is claimed under 35 U.S.C. §120. Application Ser. No. 09/463,990 is the national phase of PCT International Application No. PCT/US98/17294 filed on Aug. 21, 1998 under 35 U.S.C. §371. The entire contents of each of the above-identified applications are hereby incorporated by reference. This application also claims priority of Application No. 60/056,518 filed in the U.S. on Aug. 21, 1997 under 35 U.S.C. §119.

BACKGROUND OF THE INVENTION

This invention is in the general field of assay detection systems, such as chemiluminescent detection systems for binding assays. Various reagents and formats are used to detect an event that indicates the presence or amount of an analyte in a mixture. For example, various assays rely on the use of specific analyte binding partners to react with (bind to) the analyte. The binding event is detected in a variety of ways, often by a binding reagent that is labeled in some way with a detectable label. Immunoassays and hybridization assays are just two of the formats that use such labels. These assays can include such diverse labels as radioisotopes, colloidal gold, and enzymatic generation of a light absorbing or emitting compound. One advantage of enzymatic labels is their catalytic function—a single enzyme molecule catalytically generates many molecules of the enzyme product to be detected.

Two classes of activated acridinecarboxylic acid have been previously described: acridinecarbonyl halides and carboxylic acid anhydrides of acridinecarboxylic acid. 9-Acridine percarboxylic acid was first described in 1965 by Rauhut, Sheehan, et al at American Cyanamid (Rauhut, M. M.; Sheehan, D., Clarke, R. A.; Roberts, B. G.; and Semsel, A. M.; *Journal of Organic Chemistry*, 30, pp. 3587-3592 (1965)) as a product of the reaction between peroxide, pyridine, and 9-acridinecarbonyl chloride. Most of this paper focuses on the chemiluminescence of 9-chlorocarbonyl-10-methylacridinium chloride, but does mention that the above reaction produces chemiluminescence, that acridone was a product of the reaction, and that the chemiluminescent spectrum was consistent with acridone being the emitter. U.S. Pat. Nos. 3,352,791 and 3,539,574 issued based on this research. In U.S. Pat. No. 3,352,791 it is mentioned that 9-acridinecarbonyl chloride was first isolated by Samdahl and Weider (Samdahl and Weider, *Bull. Soc. Chim.* [5], 2, 2008 (1935)), but was not identified in that work as being chemiluminescent. 9-Acridinecarbonyl chloride was thus the first activated derivative of 9-acridinecarboxylic acid known. However, it is not very stable in water and would not be expected to be a suitable reagent for use in most diagnostic assays. In addition to claiming the acid chloride derivative of 9-acridinecarboxylic acid, the bromide and the fluoride were claimed in these two patents. They also claim carboxylic acid anhydride derivatives of 9-acridinecarboxylic acid. Derivatives of these compounds with substitutions on the acridine rings for all of these compounds are also claimed. Only some of these derivatives (for example, the fluoride and possibly sterically hindered anhydrides) would be expected to be even moderately stable in aqueous media. The main use envisioned for these compounds is as light sources in situations where other light sources might be hazardous. Cyalume light sticks are one product that resulted from this research, but they apparently use derivatives of oxalic acid rather than acridinecarboxylic acid derivatives, presumably because of a higher quantum yield.

In neither of these patents nor the paper covering this research is there any mention of using these compounds as analytical reagents. There is no discussion of whether the chemiluminescent output is proportional to $H_2O_2$ concentration. In fact, the peroxide concentrations used to produce the chemiluminescence are generally greater than 50 mM, thus well above the levels required for use in sensitive diagnostic assays. No discussion of their potential use in measuring enzyme activity was included. They do specifically refer to the lack of stability of these derivatives in aqueous media and mention that "if water is added first to the acridine compound, the peroxide should be added reasonably soon thereafter to obtain optimum results." (Sheehan, D., Clarke, R. A., and Rauhut, M. M., U.S. Pat. No. 3,352,791, column 9, lines 12 to 14). No attention was paid in the bioanalytical community to possible applications of these compounds, perhaps because of anticipated problems with stability in water. Others have examined the chemiluminescence of such compounds (White, Emil H.; Roswell, David F.; Dupont, Andrea C.; Wilson, Alan A., *Journal of the American Chemical Society*, 109 pp. 5189-5196 (1987)); of the phenyl ester of 9-acridinecarboxylic acid and of various hydrazides of 9-acridinecarboxylic acid (Rapaport, Eliezer; Cass, Malcolm W.; and White, Emil H. *Journal of the American Chemical Society*, 94 pp. 3153-3159 (1972)).

It is likely that the conditions required for initiating chemiluminescence may have discouraged further examination of these compounds as potential bioanalytical labels. Moreover, the reported quantum yield for many of these derivatives is low. Also, the success of the N-alkylacridinium esters as labels may have overemphasized the importance of substitution on the heterocyclic nitrogen of the acridine ring as a source of chemiluminescent potency. In any case no one has described the use of any of these compounds as reagents for analysis of samples containing peroxide compounds or in enzyme immunoassays or in assays using oligonucleotide probes.

Many papers and over 30 patents have previously referred to the chemiluminescence of the acridinium esters and related compounds (e.g. the sulfonamides) and much effort has been expended to design better labels or ones different enough from the original ester to be patentable. The original work on acridinium esters was done by F. McCapra's group (McCapra, Frank; Richardson, D. G.; and Chang, Y. C., *Photochemistry and Photobiology*, 4, pp 1111-1121 (1965)), and the American Cyanamid group mentioned earlier. The application of acridinium esters to immunoassays began with the publication of the synthesis and use of an acridinium ester containing an N-oxysuccinimide ester group that facilitated attachment of the acridinium ester to proteins and other biomolecules, especially those with alkylamine groups. Weeks, Ian; Beheshti, Iraj; McCapra, Frank; Campbell, Anthony K.; and Woodhead, J. Stuart, *Clinical Chemistry*, 29, pp 1474-1479 (1983). The group at the Welsh National School of Medicine received a patent covering acridinium esters as labeling reagents. (Campbell, Anthony K.; Woodhead, J. Stuart; and Weeks, Ian, U.K. Patent 2,112,779 B, (1982 Dec. 8); Campbell, Anthony K.; Woodhead, James S.; and Weeks, Ian, U.S. Pat. No. 4,946,958). Other patents which have issued directed to modified derivatives include those issued to Ciba-Corning (U.S. Pat. Nos. 4,745,181; 4,918,192; 4,927,769; 5,093,270; 5,110,932; 5,227,489; 5,241,070; 5,395,752); Abbott Laboratories (U.S. Pat. Nos. 5,468,646; 5,543,524; 5,565,570); Gen-Probe (U.S. Pat. No. 4,950,613); Mochida Pharmaceutical Co. (U.S. Pat. Nos. 5,438,139; 5,521,103; 5,594,112); Amoco (U.S. Pat. No. 5,155,216); London Diagnostics (U.S. Pat. Nos. 5,281,712; 5,283,334; 5,284,951; 5,284,952; 5,290,936; 5,321,136; 5,338,847); and Nichols Institute (U.S. Pat. No. 5,395,938). Modifications have included including groups to hinder sterically approaches to the ester group (U.S. Pat. No. 4,745,181) and thus to increase stability in aqueous media such as on the phenyl ring ortho to the ester (U.S. Pat. Nos. 4,745,181; 5,284,951) or on the acridine ring(s) peri to the ester (U.S. Pat. No. 5,321,136). Substituent groups have also been added to each of the rings to improve solubility in water (U.S. Pat. Nos. 5,227,489; 5,281,712) to make the leaving group a better leaving group or to increase the rate of attack by peroxide on the ester. Substituents have been added to the acridine ring(s) to improve the luminescent properties of the product acridone. Acridinium esters with different oxyaryl leaving groups with or without substituents have been made and so have derivatives with sulfonamide groups (U.S. Pat. No. 5,468,646) replacing the regular phenoxy leaving group. Various coupling groups have been added to the acridine ring(s), to the leaving group (the aryl or alkyl ester group or the sulfonamide group) (U.S. Pat. Nos. 5,241,070; 5,283,334), or to the alkyl or aryl group quaternizing the heterocyclic nitrogen (U.S. Pat. No. 5,438,139). The heterocyclic acridine nitrogen has also been quaternized with $O^-$, or O-alkyl (Septak, M., *J. of Biolum. and Chemilum.*, 4, pp 351-356 (1989)) Other leaving groups include hydroxamates, eneamides, thiolesters, thioesters, and activated exocyclic arylamides. Different heterocycles replacing the acridinium moiety (such as phenanthridinium and quinolinium) have been claimed. Virtually all of these groups have used acridinecarbonyl chloride derivatives in the synthesis of their modified compounds, but none have taught the use of acridinecarbonyl halides or carboxylic acid anhydride derivatives of acridinecarboxylic acid as peroxide detectors.

Several patents disclose acridan derivatives. Some of these acridans are true acridans with a hydrogen at the 9-position which require oxygen rather than peroxide for initiation of the chemiluminescent reaction or oxidation back to the acridinium form, but others are adducts which revert to the acridinium form with slight changes in condition such as addition of acid or dilution.

None of the above patents discuss the use of acridine derivatives. Some do apparently claim acridine derivatives, but in the form of the acridinium salt with the ring nitrogen protonated and carrying a positive charge (see claim 2 in U.S. Pat. No. 5,155,216, for example). Under the low pH conditions required to protonate the acridine ring nitrogen and give the acridinium form, peroxide would be virtually completely protonated and thus not a particularly good nucleophile and with the regular phenyl (or modified phenyl) ester leaving group the acridinium salt would not be expected to be very chemiluminescent. In fact the standard phenyl ester of acridinecarboxylic acid is not very chemiluminescent under most conditions. In no instance is an acridine compound discussed in examples with experimental results given.

Despite the large effort expended in the prior art to improve acridinium esters, none of these groups/companies has realized (discovered) that the activated acridinecarboxylic acid derivatives disclosed herein are useful chemiluminescent reagents.

OBJECTS AND SUMMARY OF THE PRESENT INVENTION

One object of this invention is to provide novel chemical compounds that can detect and/or measure hydrogen peroxide or other peroxide-like compounds, especially at low concentrations by means of a chemiluminescent reaction.

Another object of this invention is to provide chemical compounds that can detect and/or measure by chemiluminescence enzymes that generate hydrogen peroxide or other peroxide-like compounds directly.

Another object of this invention is to provide chemical compounds that can detect and/or measure by chemiluminescence enzymes that generate hydrogen peroxide or other peroxide-like compounds indirectly.

Another object of this invention is to provide chemical compounds that can detect and/or measure by chemiluminescence enzymes that consume hydrogen peroxide or other peroxide-like compounds.

Another object of this invention is to provide chemiluminescent assays that can be used to detect and/or measure antibodies using any of the enzymes that generate or consume, directly or indirectly, hydrogen peroxide or other peroxide-like compounds.

Another object of this invention is to provide chemiluminescent assays that can be used to detect and/or measure antigens using any of the enzymes that generate or consume, directly or indirectly, hydrogen peroxide or other peroxide-like compounds.

Another object of this invention is to provide chemiluminescent assays that can be used to detect and/or measure protein ligands using any of the enzymes that generate or consume, directly or indirectly, hydrogen peroxide or other peroxide-like compounds.

Another object of this invention is to provide chemiluminescent assays that can be used to detect and/or measure nucleic acids using any of the enzymes that generate or consume, directly or indirectly, hydrogen peroxide or other peroxide-like compounds.

Another object of this invention is to provide chemiluminescent assays that can be used to detect and/or measure polysaccharides using any of the enzymes that generate or consume, directly or indirectly, hydrogen peroxide or other peroxide-like compounds.

Another object of this invention is to provide chemiluminescent assays that can be used to detect and/or measure other biopolymers using any of the enzymes that generate or consume, directly or indirectly, hydrogen peroxide or other peroxide-like compounds.

Another object of this invention is to provide chemiluminescent assays that can be used to detect and/or measure medically important molecules using any of the enzymes that generate or consume, directly or indirectly, hydrogen peroxide or other peroxide-like compounds.

Another object of this invention is to provide chemiluminescent assays that can be used to detect and/or measure veterinarially important molecules using any of the enzymes that generate or consume, directly or indirectly, hydrogen peroxide or other peroxide-like compounds.

Another object of this invention is to provide chemiluminescent assays that can be used to detect and/or measure pharmacologically important molecules using any of the enzymes that generate or consume, directly or indirectly, hydrogen peroxide or other peroxide-like compounds.

Another object of this invention is to provide chemiluminescent assays that can be used to detect and/or measure diagnostically important molecules using any of the enzymes that generate or consume, directly or indirectly, hydrogen peroxide or other peroxide-like compounds.

Another object of this invention is to provide chemiluminescent assays that can be used to detect and/or measure forensically important molecules using any of the enzymes that generate or consume, directly or indirectly, hydrogen peroxide or other peroxide-like compounds.

Another object of this invention is to provide reagents that in the presence of hydrogen peroxide or other peroxide-like compounds generate either a glow or a flash chemiluminescent signal.

Another object of this invention is to provide reagents that are at least moderately stable in aqueous solutions or in aqueous media containing one or more detergents or similar surface active agents, including phase transfer reagents, etc. but can still react in the presence of hydrogen peroxide or other peroxide-like compounds to generate either a glow or a flash chemiluminescent signal.

Another object of this invention is to provide chemiluminescent assays including, but not limited to the types described in the previous several paragraphs that can be used to detect and/or measure diagnostically important molecules using any reactions (with organic or inorganic catalysts or with a biological catalyst or without a catalyst) that generate or consume, directly or indirectly, hydrogen peroxide or other peroxide-like compounds.

In accordance with the present invention there are thus provided stable, water soluble, acridine compounds (derivatives of 9-acridinecarboxylic acid) that react with peroxides to produce a strong and in many cases an unexpectedly long-lived chemiluminescent activity. The strength of the chemiluminescent signal from this reaction is generally correlated to the concentration of peroxide, and the signal can last long enough to provide a useful readout for assays, including those performed in aqueous systems.

The compounds therefore are useful to assay for the presence and concentration of peroxides. Various reactions can generate peroxide from reactants which themselves are the analyte of interest. For example, glucose oxidase will respond to the presence of glucose by generating peroxide. When peroxide thus produced reacts with a compound according to the present invention, the resulting chemiluminescence is indicative of the presence and concentration of glucose.

In another assay detection format, a reagent used in a binding assay is labeled with one of the elements required for generating chemiluminescence as described herein. The presence of the label is detected by adding the remaining elements. For example, an enzyme that generates $H_2O_2$ is coupled to one of the binding partners in a binding assay. After the binding assay is performed, enzyme substrate and one or more of the chemiluminescent compounds described herein are added to generate a chemiluminescent signal which indicates that the labeled binding reagent has been captured. The chemiluminescent compounds may be added before, at the same time as, or after the enzyme reaction has been started. In some cases (such as when the enzyme reaction conditions and the chemiluminescent reaction conditions are not optimally compatible) the chemiluminescent compounds may be added after the enzyme reaction.

Finally, compounds according to the invention can be used in a negative assay to detect the presence of analytes that consume peroxides, including antioxidants. For example, enzymes (or other reagents) which deplete $H_2O_2$ in the presence of a substrate can be used in an assay for the substrate by determining the loss of chemiluminescence compared to a control which includes the enzyme and a chemiluminescent compound. Similarly, the reagent that consumes peroxide (such as peroxidase or catalase) can be coupled to one of the binding partners in a binding assay. Capture of the binding partner labeled with the peroxide consuming reagent is shown by adding a solution undergoing chemiluminescence due to the reaction of peroxide and one of the chemiluminescent reagents and monitoring the loss of chemiluminescence compared to a control where the chemiluminescent solution is added to a tube without captured, labeled binding partner.

The above discussion has focused on $H_2O_2$, because it is common in biological systems. Other reactive oxygen species such as peracids, substituted peroxides including hydroperoxides, (or free radical species) can also generate chemiluminescent signal from the compounds of the invention. Reactions with peracids and substituted peroxides may generate an intermediate substituted acridine peracid derivative (AcrC(=O)OOR) which in some cases may spontaneously generate the unsubstituted, active form (AcrC(=O)OOH or AcrC(=O)OO$^-$) of acridinepercarboxylic acid, but which in other cases may require a subsequent reaction to remove the blocking substituent "R". This situation may make it easier to use these compounds to generate a flash type signal, if the reaction to remove the blocking group is sufficiently rapid.

It is important to distinguish between the following three types of acridine compounds: acridans, acridines, and acridiniums. It is easy to confuse these types of compounds because the names are used in at least two different aspects: structural form and oxidation state. Structurally, acridans have a non-aromatic central ring with two substituents at the 9-position. However, if one or both of these substituents is a nucleophile that can dissociate readily (examples include cyanide, amines, thiols, phosphate, etc.), the compound is actually an adduct form of an acridinium compound. Acridinium compounds have a positive charge on the ring nitrogen. Although it is correct to refer to the protonated form of acridine compounds with no other substituent at the heterocyclic nitrogen as acridinium salts, it is usually assumed that true acridinium compounds are substituted at the heterocyclic nitrogen with a group that does not readily dissociate. Adducts of acridinium compounds are formed by attack of a nucleophile at the 9-position. The adducts are in equilibrium with the acridinium form and their formation is easily reversed by changing conditions, such as lowering the pH, adding a reagent that lowers the concentration of the nucleophile or diluting the solution. Acridinium compounds typically give bright yellow solutions. Addition of a nucleophilic compound at a high enough concentration forms the adduct and the yellow color disappears, an indication that the predominant form is the acridan adduct form. Lowering the concentration of the nucleophile generally restores the yellow color. At the pH's where the acridine heterocyclic nitrogen is protonated (pH < about 5), few good nucleophiles are unprotonated, so adducts of acridine compounds without a covalent substituent on the ring nitrogen are unusual. Reduction of acridinium compounds gives true acridan compounds which can be distinguished from the adduct forms by having a hydrogen at the 9-position. This proton is dissociable but as an electrophile (in aqueous media as $H_3O^+$) not as a nucleophile. In fact the acridan anion resulting from dissociation of this proton is a nucleophile. In aqueous media dissociation of hydride from acridan compounds would not be a likely event. Other "true" acridans would include acridans with two nondissociating groups at the 9-position or with another electrophilic substituent (e.g. Li or Mg) in place of the proton.

DETAILED DESCRIPTION OF THE INVENTION

Figure 1:
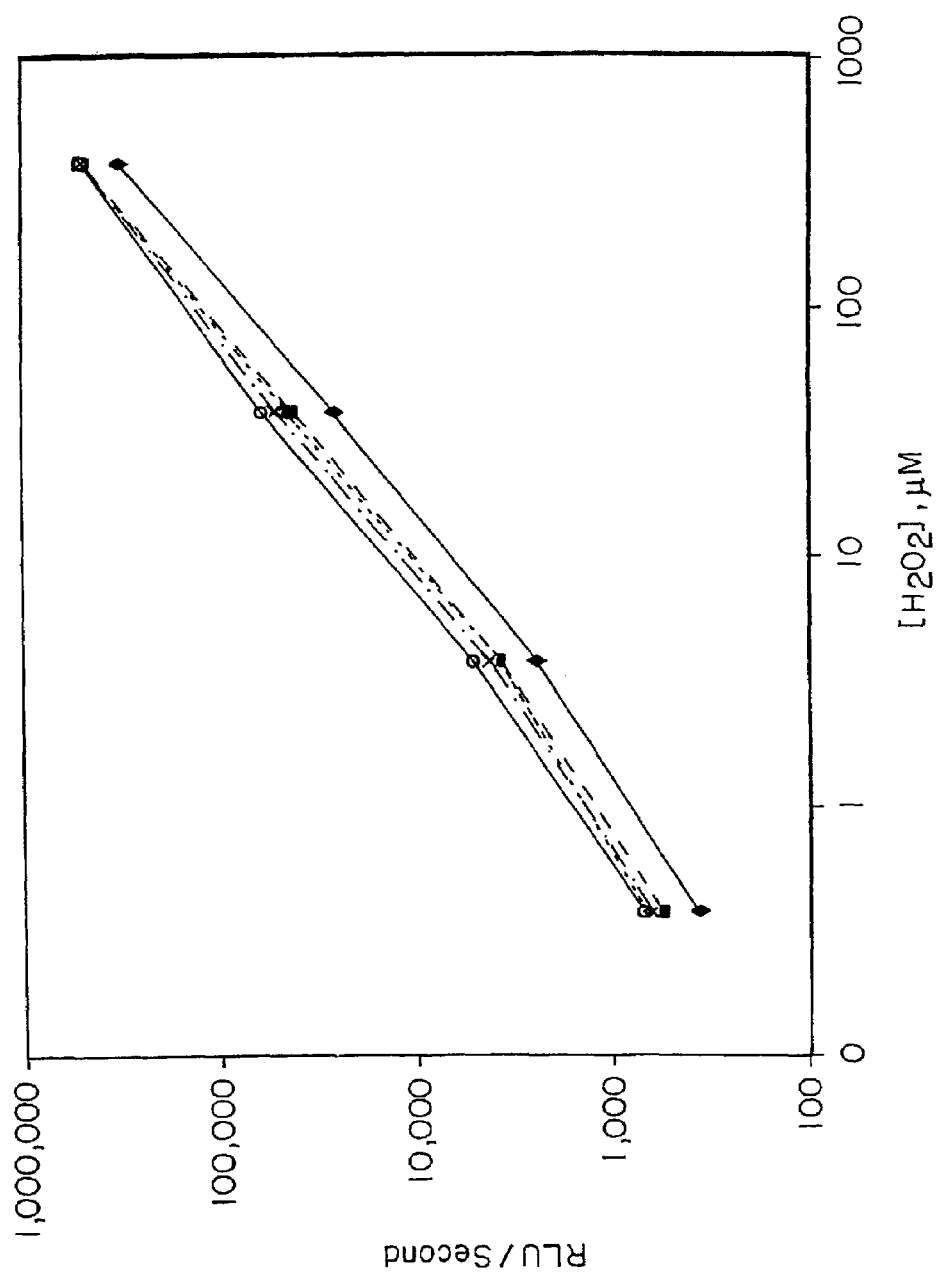
FIG. 1 depicts the chemiluminescent signal from 9-acridinecarbonylimidazole as a function of the concentration of hydrogen peroxide in the indicated glucose oxidase buffer. The different calibration lines are for various times after addition of hydrogen peroxide.

A new family of chemiluminescent reagents are disclosed herein which are useful for detection and measurement of peroxides and other peroxide-like species, including some other reactive oxygen species.

Since many enzymes can generate peroxide directly or can, with appropriate substrates, produce peroxide indirectly, among the more useful applications of these chemiluminescent reagents are chemiluminescent assays for nucleic acids and chemiluminescent immunoassays using one of these peroxide-generating enzymes as labels. Enzymes that generate peroxide directly include, but are not limited to, (1) glucose oxidase, (2) xanthine oxidase, (3) cholesterol oxidase, and (4) glycerol phosphate oxidase. Enzymes that generate peroxide with an appropriate substrate include, but are not limited to, (1) alkaline phosphatase with BCIP (5-Bromo-4-Chloro-3-Indolyl Phosphate, also known as X—P or X—PO$_4$), (2) β-galactosidase with BCI-galactoside (or X-gal), (3) β-glucuronidase with X-glucuronide, and (4) many other esterases with the corresponding X-ester (many of which are available commercially). Negative assays are also possible with enzymes that consume peroxide such as peroxidases and catalases. Alkaline phosphatase and horseradish peroxidase are currently the two most frequently used enzymes in enzyme immunoassays and nucleic acid probe assays. Just behind these two enzymes in popularity of use are glucose oxidase, β-galactosidase, β-glucuronidase, and xanthine oxidase. The reagents disclosed herein can be used to monitor the activity of any of these enzymes.

Enzyme Immunoassays and Nucleic Acid Probe Assays

The most frequently used enzymes for enzyme-based assays for antibodies and for nucleic acid probes are horseradish peroxidase (HRP), alkaline phosphatase (AP), and β-galactosidase. (Mayer, Andreas and Neuenhofer, Stephan, *Angew. Chem. Int. Ed. Engl.*, 33, pp 1044-1072 (1994)). Conjugates of these three enzymes with antibodies, biotin, streptavidin, avidin, etc. are available commercially. For chemiluminescence based assays the more popular systems are the enhanced chemiluminescent system using luminol and peroxidase developed by Kricka, et al, several luciferase systems and the dioxetane substrate derivatives developed by Irena Bronstein and others at Tropix using alkaline phosphatase, β-galactosidase and β-glucuronidase as the enzyme with the appropriate substrate. Newer systems are emerging such as the use of xanthine oxidase. See Tijssen, P., *Practice and Theory of Enzyme Immunoassays*, pp 173-219 (1985) Elsevier Science Publishers B. V. for properties of many of these enzymes and for a discussion of the properties of an ideal enzyme label.

Applications of Acridine Reagents and Comparisons to Other Systems

In addition to being used as a label attached to an antibody, antigen, or probe, HRP is often used to measure peroxide produced by other enzymes in assays for cholesterol (using cholesterol oxidase), for glucose (using glucose oxidase) for triglycerides (using glycerol phosphate oxidase), and other diagnostically important molecules. The reagents disclosed herein can be used in these situations where horseradish peroxidase and colorimetric, fluorimetric, or chemiluminogenic substrates are currently used. Typical colorimetric HRP substrates include 3,3',5,5'-tetramethylbenzidine (TMB) 3,3'-diaminobenzidine, Trinder reagents, etc. Luminol in the presence of enhancers is the substrate of choice for chemiluminescent detection of HRP. The disclosed system offers several advantages over these peroxidase systems:

1. Only the detection reagent need be added rather than an enzyme (peroxidase), a detection reagent (luminol or other substrate) and enhancers.
2. To detect luminol a high pH is usually required; these acridine reagents can be used over a wide pH range including acid pH's; this would make simpler formats possible and make possible assays that were previously difficult to design.
3. The mechanism of the peroxidase luminol system is complex and even after decades of study is not completely understood. In contrast, the mechanism for light production from the acridine reagents appears to be much simpler, making it easier to anticipate the effects of various contaminants or other assay components.
4. One of the limitations of peroxidase is that its activity dies during a typical assay. By eliminating peroxidase this problem is avoided. There is no indication that any of the byproducts at the concentrations formed in a typical reaction interfere with further detection or with a repeat assay. The chemiluminescent signal from many of the reagents disclosed herein typically lasts for hours and in some cases for days.

The dioxetanes have found most use in blot or membrane formats but are not as useful in solution formats. To achieve better sensitivity enhancers must be added. Like the dioxetanes, many of these acridine reagents give "glow" kinetics (long lived chemiluminescent signal) and there are compounds such as detergents and organic solvents that can enhance the signal for these reagents. Solution formats work well with the disclosed reagents. The reagents, however, do not have to be redesigned for each enzyme like the dioxetanes. Depending on the enzyme being detected an auxiliary reagent (BCIP or BCI-gal, for example) may be required, but many of these are available commercially. The disclosed reagents complement the dioxetanes, but have a broader range of application and can detect a wider variety of enzymes as discussed earlier.

Negative Assays

Peroxidase and Catalase

Though not yet a popular enzyme for immunoassays, catalase has many properties that make it attractive for such applications, especially its high turnover number (one of the highest known: 40 million per second). (Creighton, Thomas E., *Proteins*, p 407 (1984) W. H. Freeman and Company). Peroxidase and catalase consume peroxide. A negative assay using one of the acridine reagents for either of these enzymes is workable. The dynamic range suffers compared to the positive assays with these reagents, but because the chemiluminescent signal persists for a very long time and can be formulated to be a virtually constant signal in the absence of peroxidase, one can vary the operating range of the assay by changing the peroxide concentration used to establish the plateau signal level. Peroxidase or catalase can also be used as a reagent to reduce the background signal in a positive assay.

Alkaline Phosphatase and β-Galactosidase

In addition to being a very popular enzyme for immunoassays alkaline phosphatase is almost certainly the most popular enzyme for use in nucleic acid probe assays. One of the most popular substrates for alkaline phosphatase, BCIP (5-Bromo-4-Chloro-3-Indolyl Phosphate), following removal of the phosphate group (to give BCI, initially) can react with oxygen to generate hydrogen peroxide and an indigoid dye. (Arakawa, H.; Maeda, M.; Tsuji, A. *Analytical Biochemistry*, 199, pp 238-242 (1991)). This indirect method of generating peroxide should also work for the other enzymes for which BCI (or other indigo- or quinol-like) substrates are available including β-galactosidase, β-glucuronidase, and several other esterases. With the appropriate BCI substrate, assays for any of these enzymes with activated acridinecarboxylic acid derivatives are possible. Recently a new class of similar indolyl substrates has been developed (U.S. Pat. Nos. 5,364,854 and 5,364,767). The red-$PO_4$, red-gal, etc. substrates react similarly and could also be used to generate peroxide with the appropriate enzyme. Obviously, any substrate for a hydrolase that can be considered as a protected form of a compound that with the protective group removed by enzymatic action readily produces peroxide (usually, but not limited to, reaction with oxygen) would be an appropriate substrate for use in assays that are the subject of this disclosure. For example, anthrahydroquinones are well known as commercial sources for the synthesis of hydrogen peroxide; they readily reduce oxygen to give hydrogen peroxide and anthraquinones. Phosphorylation of the anthrahydroquinone would give a protected derivative that would be a substrate for alkaline phosphatase. An anthrahydrogalactoside would be suitable for use with β-galactosidase, etc.

Several enzymes (oxidases) are known that produce peroxide directly and many are commercially available. Xanthine oxidase and glucose oxidase (GOase) are two oxidases that have been used in immunoassays. (Kricka, L. J., *Clinical Chemistry*, 37, pp 1472-81 (1991)). With glucose oxidase and the imidazolide of 9-acridinecarboxylic acid present throughout the reaction one can detect about 10 attomoles (1 attomole is $10^{-18}$ moles or about 600,000 molecules) of glucose oxidase. Glucose oxidase is used in many clinical assays to monitor glucose for diabetes management. In laboratories where several other chemiluminescent assays are being run on a patient sample, assays using one of the activated derivatives of 9-acridinecarboxylic acid to measure the hydrogen peroxide produced should be a feasible alternative to currently used methods. Two other oxidases that are employed in clinically relevant assays to produce peroxide are cholesterol oxidase for monitoring cholesterol and glycerol phosphate oxidase for measuring triglycerides. While horseradish peroxidase (HRP) systems are currently the most popular bioanalytical methods used to measure $H_2O_2$, the acridine reagents described herein offer several advantages.

Other Applications

In addition to being used in probe assays and immunoassays β-galactosidase, β-glucuronidase, and secreted placental alkaline phosphatase are often used as reporter genes in molecular biology studies. The dioxetanes developed by Tropix, Inc. (Bedford, Mass.) have been adapted to monitor the expression of these genes by chemiluminescence. (Bronstein, Irena; Fortin, John; Stanley, Philip E.; Stewart, Gordon S. A. B.; and Kricka, Larry J., *Analytical Biochemistry*, 219, pp 169-181 (1994)). Activated forms of 9-acridine carboxylic acid should also be adaptable to such applications. In clinical laboratories it is important that an instrument can be used in a wide range of assays. The more assays in the menu the easier it is to get the laboratory to adopt a particular approach and purchase or rent the instrument and use your assays and reagents. In addition to oxidases and the enzyme labels discussed earlier it should also be possible to monitor the activity of most dehydrogenases since methods to couple dehydrogenase activity to the production of hydrogen peroxide are known (Kricka, L. J., *Clinical Chemistry*, 37, pp 1472-81 (1991)). One other potential use of these compounds is to detect hydrogen peroxide in cells. There is recent speculation that peroxide is an intracellular second messenger. (Sundaresan, Maitrayee, Yu, Zu-Xi, Ferrans, Victor J., Irani, Kaikobad, Finkel, Toren, *Science*, 270, pp 296-299 (1995)). Some of these acridine derivatives can enter cells and be used to monitor intracellular levels of peroxide. By using a different leaving group the properties of the detection reagent can be adapted to fit a particular application. These properties include charge, solubility, stability in the reaction medium, and kinetics of displacement by peroxide.

Suitable Acridinecarboxylic Acid Derivatives

The novel reagents of the present invention are activated derivatives of acridinecarboxylic acid, many of which are surprisingly stable in aqueous solutions. The novel reagents also react over a wide range of pH's with nucleophilic peroxide compounds and generate a chemiluminescent signal, presumably by first forming acridinepercarboxylic acid and then decomposing to give acridone and emit light. The amount of chemiluminescence is directly proportional to the peroxide concentration over several orders of magnitude. Several classes of activated acridinecarboxylic acid exist. Among these are two classes that have been previously described as chemiluminescent but have not been used previously as analytical reagents to measure the concentration of peroxide compounds or to monitor enzyme activity for enzymes that generate or consume peroxide compounds directly or indirectly.

These two classes are the acridinecarbonyl halides and carboxylic acid anhydrides of acridinecarboxylic acid. Among the new classes shown to be useful chemiluminescent reagents are active esters of 9-acridinecarboxylic acid (examples include but are not limited to esters formed by coupling 9-acridinecarboxylic acid with N-hydroxysuccinimide (NHS), 1-hydroxybenzotriazole (HOBt), dinitrophenol (DNPOH), or ethyl cyanoglyoxylate-2-oxime (ECGO)); active amides of 9-acridinecarboxylic acid (examples include but are not limited to imidazolide, triazolide, and tetrazolide); active sulfonamides of 9-acridinecarboxylic acid; and the silyl esters of 9-acridine carboxylic acid.

Acridinecarboxylic acid derivatives suitable for use in the present invention may be defined by the formula

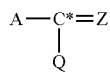

where C* is an sp2 co-ordinated carbon atom;

A is a 9-acridinyl or substituted 9-acridinyl moiety;

Z is a moiety that is covalently bonded to C* including, but not limited to O, S, N—$R^1$, or $^{\oplus}$N—$R^1R^2$ where $R^1$ and $R^2$ can be independently chosen from hydrogen, alkyl, alkoxy, aryl, alkylaryl, heteroaryl, or heteroalkoxy moiety, each of which may be substituted or unsubstituted. Preferably, the alkyl and alkoxy moieties contain from 1 to 5 carbon atoms.

It will be obvious to those skilled in the art that activated derivatives of 9-acridinecarboxylic acid with one or more substituents on either of the outside aromatic rings (at positions 1, 2, 3, 4, 5, 6, 7, or 8 in the current acridine numbering scheme) will react similarly to the unsubstituted activated 9-acridinecarboxylic acid compounds. Thus unsubstituted, singly, or multiply substituted 9-acridinecarboxylic acid compounds are all intended to fall within the scope of the present invention. Compounds with additional rings, attached to or fused with, either or both of these outside rings are also contemplated. Thus, for example, A can be

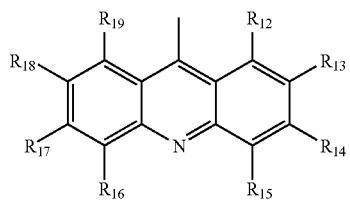

where $R_{12}$ through $R_{19}$ can be independently chosen from hydrogen, alkyl, alkoxy, aryl, alklaryl, heteroaryl, heteroalkoxy, aldehyde, keto, amino, nitro, halo, sulfate, sulfonyl, carboxy, carboxyester, phosphate, or phosphoester, each of which may be substituted or unsubstituted. Preferably, the alkyl and alkoxy moieties contain from 1 to 5 carbon atoms. Any two of $R_{12}$ through $R_{19}$ can be part of a cyclic structure which may be aromatic or not and may contain any small number of heteroatoms.

Q is selected to be a suitable leaving group under aqueous or mixed aqueous-organic conditions (including, but not limited to detergent solutions, polar solvent mixtures, emulsions and multiphase systems) to yield a compound which exhibits chemiluminescent properties in the presence of a peroxide or peroxide-like compound.

Compounds with suitable leaving (Q) groups include but are not limited to nitroaryl esters, halogenated aryl esters, oxysuccinimide esters oxybenzotriazole esters, imidazolides, triazolides, tetrazolides, pyridine amides, silyl esters, eneamides, and sulfonamides.

Examples of suitable leaving groups (Q) include but are not limited to the following: (1) N-linked optionally substituted heterocyclic aryl moieties such as imidazole, oxazole, thiazole, pyrazole, pyrimidine, purine, quinoline, isoquinoline, pyrrole, indole, pyridine, tetrazole, triazole, benzotriazinone, N-oxysuccinimide, oxyphthalimide, or carbazole moieties; (2) O—N=C(CN)—CO—$R^3$ where $R^3$ is an alkoxy, substituted alkoxy, sulfhydryl, alkyl or substituted alkyl group, where $R^3$ as alkoxy may be O—$R^4$ where $R^4$ is an optionally substituted alkyl or substituted alkyl group where the alky group preferably has from 1 to 5 carbon atoms; (3) O—Ar, where Ar is an aromatic or heteroaromatic cyclic moiety substituted with at least one electron withdrawing element or which when unsubstituted is a leaving group which can readily be displaced by hydrogen peroxide or an anion derived from hydrogen peroxide (such as optionally substituted phenyl, optionally substituted pyridinyl, dinitrophenyl or chloropyridinyl);

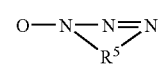
(4)

where $R^5$ is part of a single cyclic or multicyclic heterocyclic moiety; (5) O—N=C(CN)—Ar where Ar is an aromatic or heteroaromatic moiety;

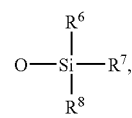
(6)

where $R^6$, $R^7$, and $R^8$ can be independently chosen from among alkyl, alkoxy, aryl, alkylaryl, heteroaryl, or heteroalkoxy moieties, each of which may be substituted or unsubstituted; (7) S—$R^9$ where $R^9$ is alkyl, alkoxy, aryl, alkylaryl, or heteroaryl moiety, each of which may be optionally substituted; (8) halide or pseudohalide (such as fluoride),

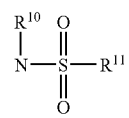
(9)

where $R^{10}$ and $R^{11}$ can be independently chosen from alkyl, aryl, alkylaryl, or heteroaryl, moieties, each of which may be optionally substituted (e.g., $CF^3$).

In the above, each of the above alkyl or alkoxy moieties preferably contain from 1 to 5 carbon atoms.

More specifically, the following leaving groups have been found to be useful in the practice of the present invention:

(1) ethyl cyanoglyoxylate-2-oxime

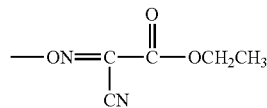

(2) 2-hydroxyimino-2-phenylacetonitrile

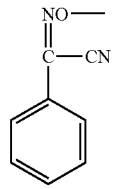

-continued (3) 3-hydroxy-1,2,3-benzotriazin-4(3H)-one

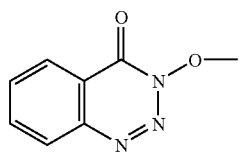

(4) 1-hydroxybenzotriazole

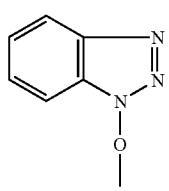

(5) N-hydroxysuccinimide

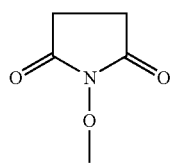

(6) 6-chloro-2-pyridinol

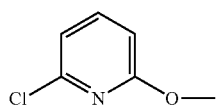

(7) 2,4-dinitrophenol

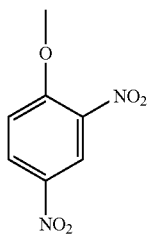

(8) 4-hydroxy-3,5-dinitrobenzoic acid

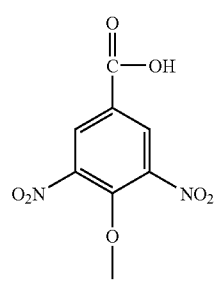

(9) imidazole

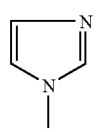

-continued

(10) N-alpha-acetyl-L-histidine

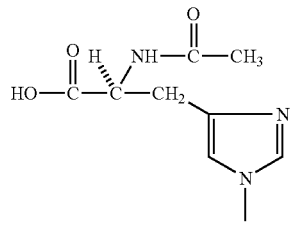

(11) 1,2,4-triazole

(12) 2,3,5,6-tetrafluoro-4-hydroxybenzoic acid

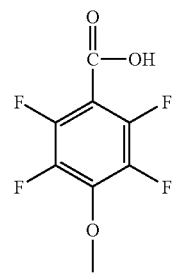

(13) 1-methylimidazole

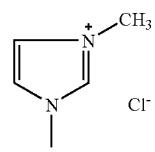

(14) 4,5-dicyanoimidazole

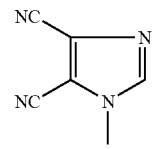

(15) 1H-tetrazole

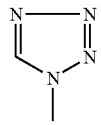

The dash in the preceding structure diagrams indicates the presumed site of attachment of the indicated Q to the sp2 co-ordinated carbon, C*. In some cases there are two or more sites on Q which could from the bond to this C*. Examples include (10) N-alpha-acetyl-L-histidine, (11) 1, 2, 4-triazole, and (15) 1H-tetrazole. The site indicated is the one expected on chemical grounds either for steric reasons or from structural determinations of related compounds as described in the chemical literature. In some cases there may even be a mixture of products formed during synthesis. Should subsequent analysis indicate that the bond to C* is to a site not shown, this does not invalidate any of our claims on that compound. The structure diagrams are for illustrative purposes only.

Among the advantages of chemiluminescent detection systems in general over calorimetric and fluorimetric systems are sensitivity (subfemtomole sensitivities for the target species are not unusual), low backgrounds, and wide dynamic range.

The acridinium esters are usually used as direct chemiluminescent (CL) labels, covalently attached to the antibody or nucleic acid probe. With standard reagents for initiating CL the kinetics are of the "flash" type, giving a brief burst of CL usually in less than 10 seconds. This makes possible the rapid, very sensitive assays that are characteristic of acridinium ester assays. For such assays the luminometer must have one or more injectors and the injection force must also insure good mixing. This can be difficult or expensive for a multiple well plate reading instrument. With the present system the glow kinetics can be initiated outside the instrument without sacrificing light yield or precision. By initiating acridinium ester chemiluminescene at lower pH's (< about 10.5) glow kinetics are possible, but care must be taken in buffer choice and buffer concentration. Acridinium esters form adducts with most nucleophiles including the base form of most buffers except borate. This can complicate assay design and reproducibility. Also, the glow kinetics with acridinium esters at these low pH's (< about 10.5) is not a plateau, as with the acridinecarbonylimidazole, but a fast rising peak with a slow decay making timing more critical. Since neither acid (to revert acridinium ester adducts formed during an assay) nor base (to get pH >10.5) is needed to initiate light emission with the present reagents fewer hazards are associated with this system. Moreover being a direct label that is destroyed by detecting it, the only way to verify a questionable result with acridinium esters is to retain some of the sample for a repeat assay. With the present system the persistence of the signal makes it possible to recheck immediately any questionable or unexpected result. Sample contributions to background will likely be less with the lower pH of initiating chemiluminescence.

Methods of Preparation

The activated derivatives of 9-acridinecarboxylic acid are easily synthesized by standard methods in organic chemistry. For example, the imidazolide can be made by (1) dissolving the carboxylic acid in pyridine and adding carbonyldiimidazole (CDI), (2) by converting the carboxylic acid to the carbonyl chloride with thionyl chloride, purifying the carbonyl chloride and reacting it with imidazole. Another way is to react the carboxylic acid with a carbodiimide (dicyclohexylcarbodiimide-DCC or diisopropylcarbodiimide-Dipc) and imidazole. The thionyl chloride route is probably the most convenient for several reasons. The reagent is easily removed by boiling it off The product carbonyl chloride can then be dissolved in an appropriate solvent and reacted with one or, in separate reactions, with several leaving groups. The disadvantage of this route is that the carbonyl chloride is sensitive to water hydrolysis. If the tetramethyluronium derivative of the desired leaving group is available (NHS and HOBt derivatives are) or is synthesized first, it can be reacted with the carboxylic acid directly or its salt form to give an activated derivative.

More specifically, 9-acridinecarbonylimidazole may be made by the following method. To a 4 mL glass vial was added 93.8 mg of 9-acridinecarboxylic acid, hydrate (Aldrich #24,634-4, FW=223.23, 97%—effective MW=230.134) (408 micromoles) and 2 mL of thionyl chloride (Aldrich #23,046-4, FW=118.97, 99%, density=1.631) (27.1 millimoles=66.6 times the amount of 9-acridinecarboxylic acid). The mixture was refluxed at about 85 degrees C.; after a short time at reflux the mixture clarified. After 4 hours at reflux the condenser was removed and the excess thionyl chloride was removed by evaporation at 85 degrees C., leaving a yellow crystalline residue. After cooling, the vial was capped, sealed with parafilm to provide extra protection from moisture and stored at −20 degrees C. According to the literature the residue is the hydrochloride salt of the desired 9-acridinecarbonyl chloride.

Just prior to use, the vial was allowed to warm to room temperature, before adding 4.0 mL acetonitrile (stored over molecular sieves to reduce moisture content). Some of the residue dissolved to give a yellow to orange solution of the hydrochloride salt of 9-acridine carbonyl chloride. One mL of this solution was added to 200 uL of 1.0 M imidazole in $CH_3CN$. The addition of the imidazole quickly made the solution almost colorless, indicating neutralization of the hydrochloride salt. The reaction was allowed to proceed at room temperature. Subsequent HPLC analysis showed virtually complete conversion to the 9-acridinecarbonyl imidazolide.

The acetonitrile solution of 9-acridinecarbonyl chloride can be used to form other conjugates, esters, or amides. The resulting products can then be screened for chemiluminescence, thereby testing these other potential leaving groups. For example, to 50 uL of this solution (containing approximately 5 micromoles of the activated acridine derivative) can be added a solution of the desired leaving group, preferably in acetonitrile or N,N-dimethylformamide (DMF) containing an excess of the leaving group, preferably at least 2 to 20 times the molar amount of carbonyl chloride (10 to 100 micromoles in this example). In those cases where the leaving group is in its protonated form it is also helpful to add enough of a poorly nucleophilic base such as pyridine to deprotonate the leaving group and to neutralize the hydrochloride salt of the acridinecarbonyl chloride (in this example approximately 125 micromoles of pyridine was used.) As the base is added, the original orange solution becomes yellow and then pale yellow (unless the solution of the leaving group is also colored), indicating that the acridine ring is less protonated. If the solution becomes colorless, the reaction may proceed even better, but may also be more sensitive to hydrolysis from any adventitious water that may be present in the solution. The moderate pKa of pyridine (and of imidazole in the previous example) help keep the pH from getting too high. After reacting for the desired time period (anywhere from minutes to days), the reaction can be tested directly for chemiluminescence simply by adding an aliquot to a solution of peroxide in the desired medium. For example, a small aliquot of a reaction can be added to a solution of 40 uM $H_2O_2$ in 50 mM sodium phosphate buffer at pH near 8.2 and the chemiluminescence measured over time; this is a good concentration of peroxide for screening purposes, but higher or lower concentrations can also be used. It is important to include a control reaction without a leaving group added, but with any base used added, since any peroxide present in the solvents used for the reactions will form the percarboxylic acid directly and will chemiluminesce. Another control that should be run is to add an aliquot of the reaction to the medium without added peroxide and monitor the chemiluminescence and later add peroxide. This control indicates if the product is stable in the chosen medium for long enough periods to be useful. The length of time between adding the reagent and adding the peroxide will depend on the requirements of the application and can be varied as desired. The chemiluminescence observed before adding peroxide is an indication of the amount of peroxide present in the reaction solvents and/or the components of the testing medium.

Examples

1. Reaction with Hydrogen Peroxide

Figure 2:
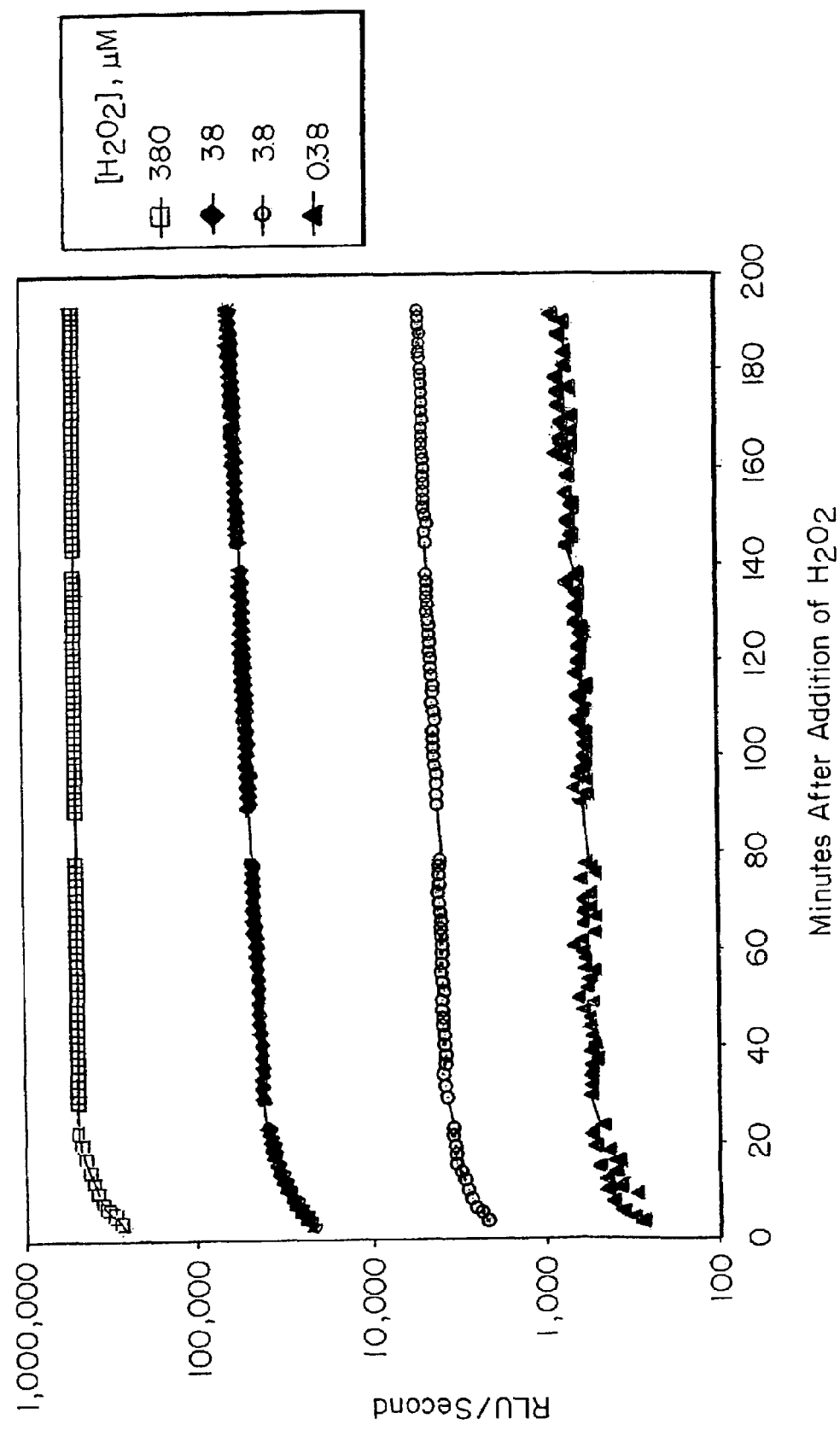
FIG. 2 shows the kinetics of the chemiluminescent signal development as a function of time after addition of hydrogen peroxide. The different curves represent the data from samples with different amounts of hydrogen peroxide added.

In FIGS. 1 and 2 are shown the chemiluminescence of the imidazolide of 9-acridinecarboxylic acid upon reaction with different levels of hydrogen peroxide concentration in a medium suitable for monitoring glucose oxidase activity. Both the kinetics of signal development and the variation of signal intensity as a function of peroxide concentration are shown. Note that the non-time axes are logarithmic and that the signal reaches a virtual plateau within 30 minutes after addition of the peroxide.

Protocol for FIGS. 1 and 2:
Luminometer: BMG Lumimaster Plate Reader
Signal noise in the range of 50 to 100 RLU/second To each well is added 100 uL of premix. Read the chemiluminescence several times. Add 5 uL hydrogen peroxide in 10 mM NaPi buffer (pH=pKa). Read chemiluminescence over several hours.

Each well contained 100 uL of solution comprised of 50 mM in $NaPO_4$. (pH=8.2), 1.50% (w/v) glucose; 5.0% (v/v) DMF; 2.0% (v/v) Triton X-100; 210 uM Acl. The chemiluminescence was read several times prior to adding 5 uL hydrogen peroxide. The hydrogen peroxide was added in the following amounts (in picomoles): (1) 40,000, (2) 4,000, (3) 400, (4) 40.0, and (5) 0.00. Data shown are averages of two wells for the hydrogen peroxide samples and of eight wells for the blank. The lines in FIG. 1 represent the calibration at different times after addition of hydrogen peroxide.

2. Chemiluminescent Detection of Glucose Oxidase

Figure 3:
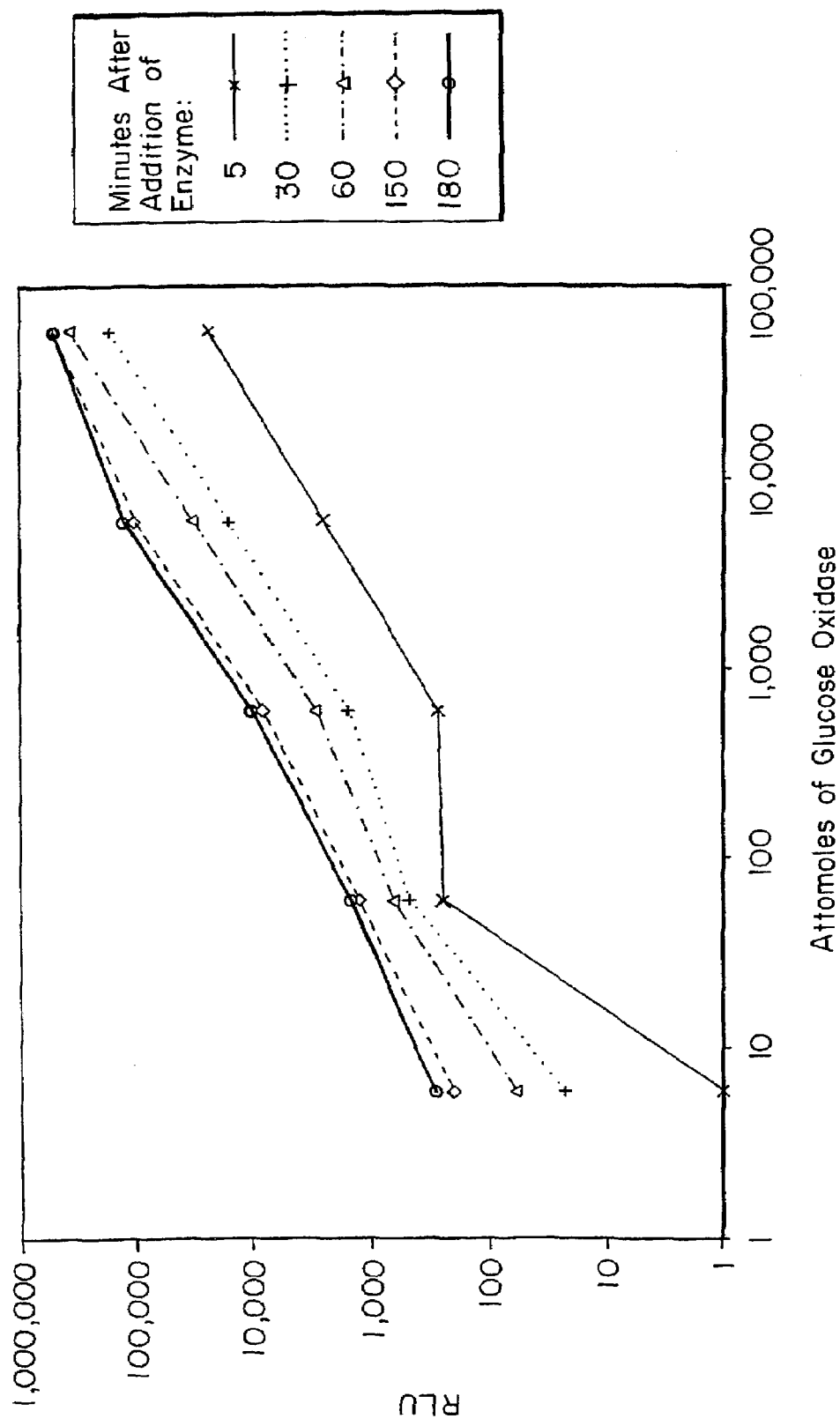
FIG. 3 depicts the results from a second experiment plotted to show the calibration at various times after addition of different amounts of glucose oxidase to the indicated buffer containing 9-acridinecarbonylimidazole.
Figure 4:
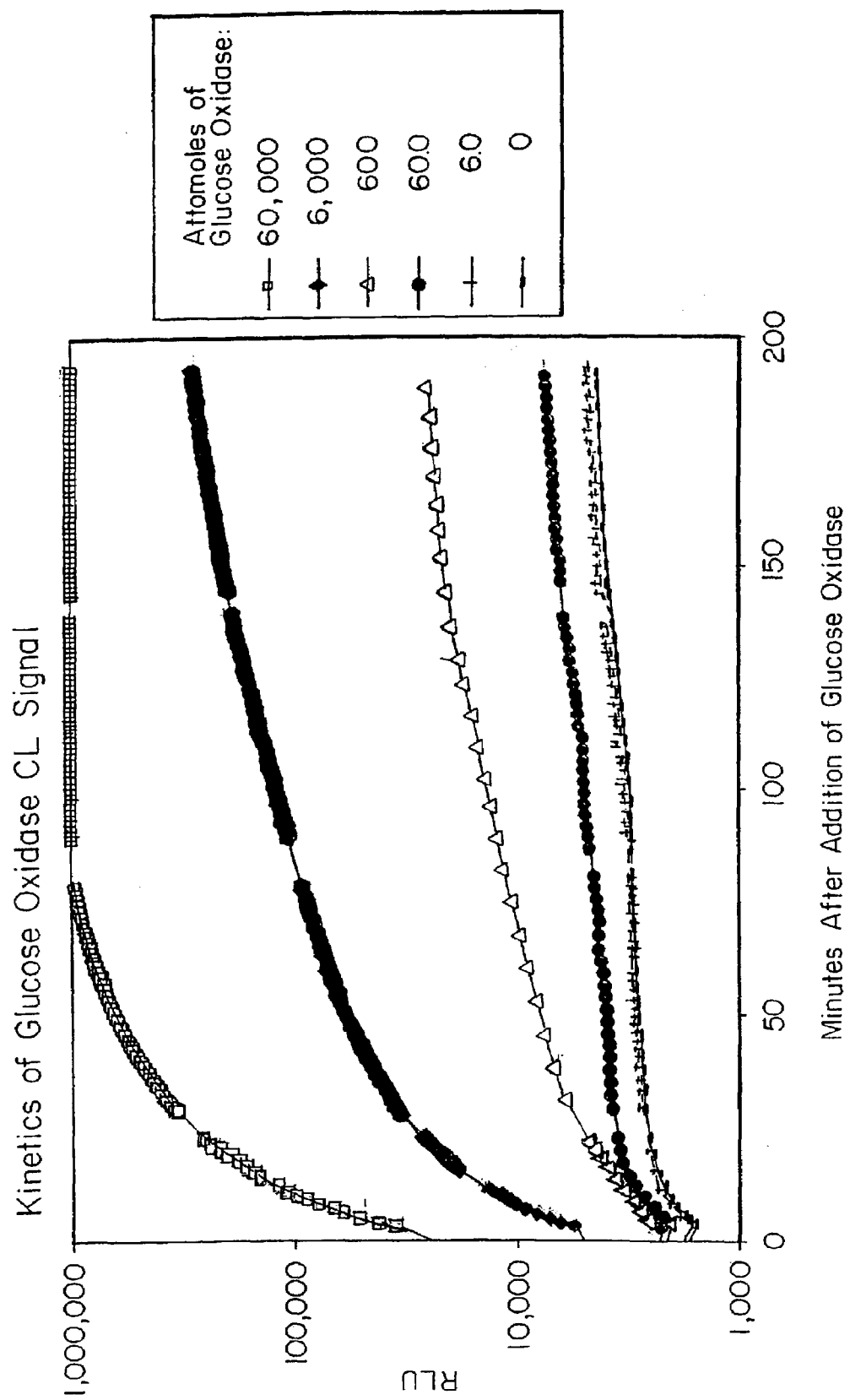
FIG. 4 shows the kinetics of chemiluminescent signal development with the indicated amounts of glucose oxidase added.

In FIGS. 3 and 4 are shown the calibration of glucose oxidase over 5 orders of magnitude. Note that the reaction conditions for FIGS. 3 and 4 are the same as in FIGS. 1 and 2. The detection limit for glucose oxidase in this experiment is about 10 attomoles in a 105 μL reaction.

Protocol for FIGS. 3 and 4:
Luminometer: BMG Lumimaster Plate Reader
Signal noise in the range of 50 to 100 RLU/second To each well is added 100 uL of premix. Read the chemiluminescence several times. Add 5 uL glucose oxidase in 10 mM NaPi buffer (pH=pKa). Read chemiluminescence over several hours.

Each well contained 100 uL of solution comprised of 50 mM in $NaPO_4$. (pH=8.2), 1.50% (w/v) glucose; 5.0% (v/v) DMF; 2.0% (v/v) Triton X-100; 210 uM Acl. The chemiluminescence was read several times prior to adding 5 uL of glucose oxidase. The glucose oxidase was added in the following amounts (in attomoles): (1) 60,000, (2) 6,000, (3) 600, (4) 60.0, (5) 6.00 and (6) 0.00. Data shown are averages of two wells for the glucose oxidase samples and of eight wells for the blank.

3. Chemiluminescent Detection of Alkaline Phosphatase

Figure 5:
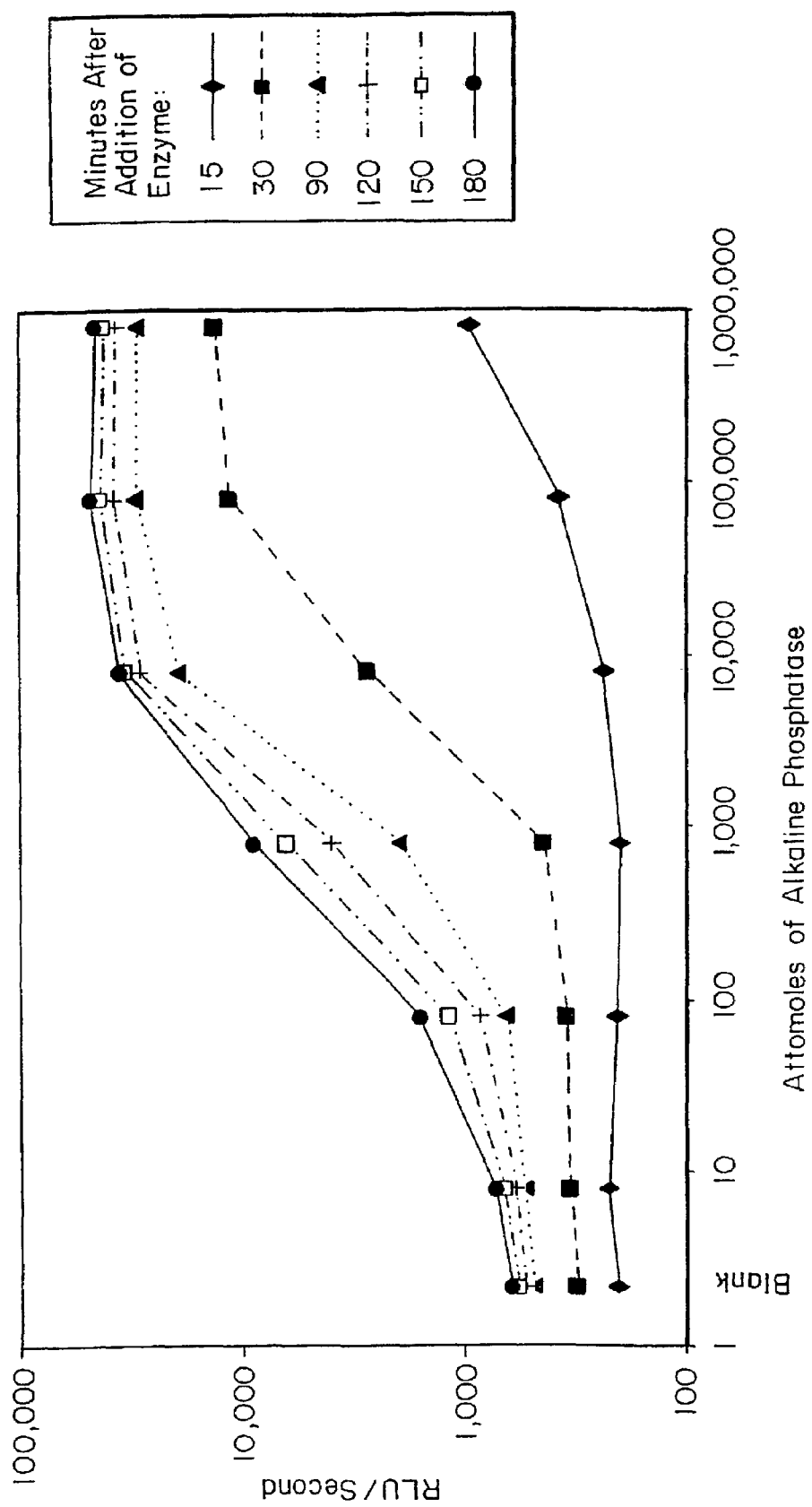
FIG. 5 shows the chemiluminescent calibration curves for a third experiment: detection of alkaline phosphatase at the indicated times after addition of the alkaline phosphatase to an appropriate buffer containing 9-acridinecarbonylimidazole.
Figure 6:
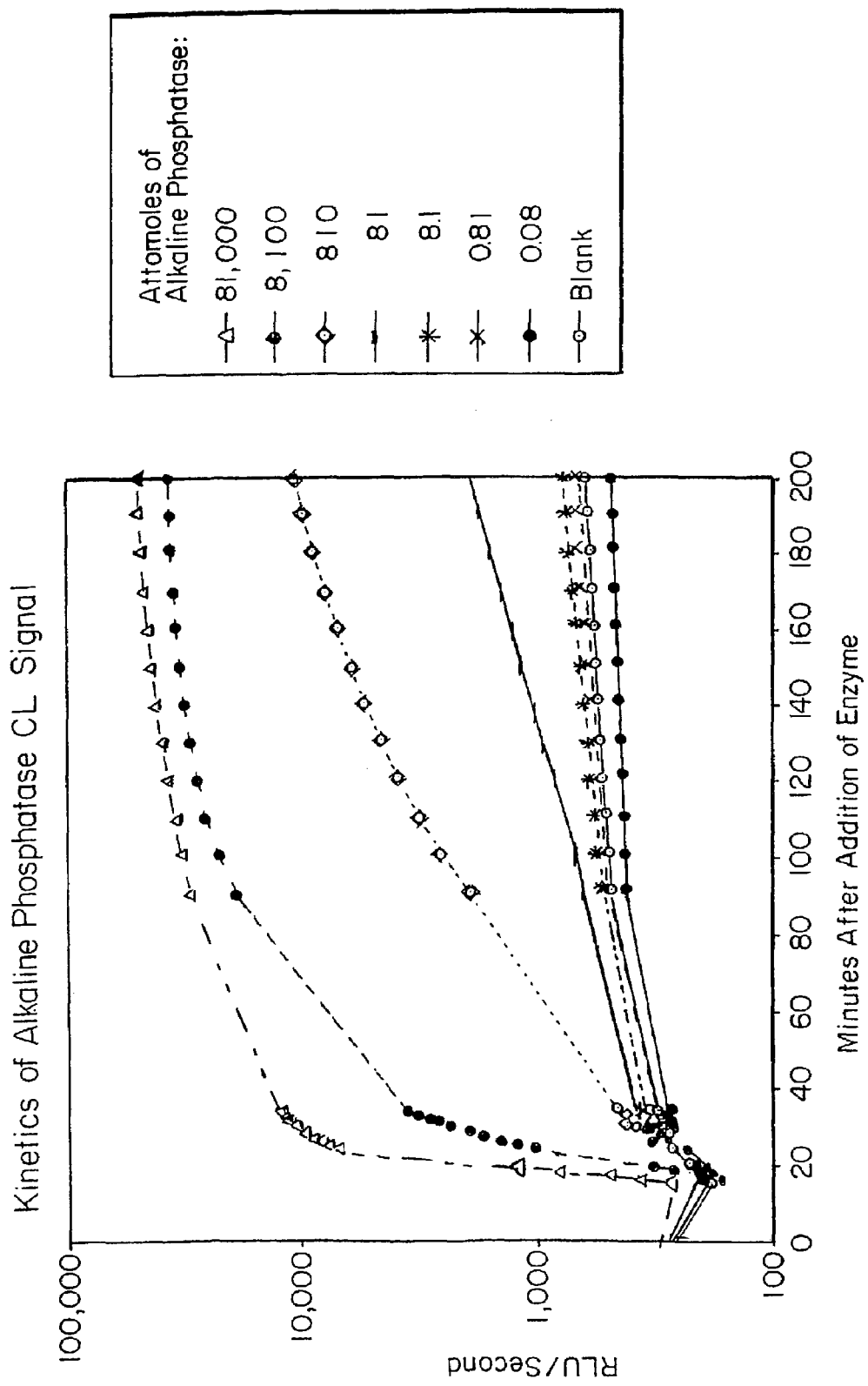
FIG. 6 shows the kinetics of the signal development for addition of the indicated amounts of alkaline phosphatase.

In FIGS. 5 and 6 are shown the kinetics and the concentration dependence of chemiluminescent signal generation with alkaline phosphatase and with BCIP as the substrate which after cleavage of the phosphate group reacts with oxygen to produce hydrogen peroxide. Here the detection limit is about 8 attomoles of enzyme. In the calibration graph the blank readings have been plotted (arbitrarily) in this region to show that this enzyme level gives signal above the blank signal. Most of the blank signal is from peroxide impurities in the detergent stock. The downward slope in the kinetic graph upon addition of enzyme can be explained by two factors. The BSA (bovine serum albumin) the enzyme buffer reacts with this peroxide and dilution also causes a small drop in signal intensity.

Protocol for FIGS. 5 and 6:
Luminometer: BMG Lumimaster Plate Reader
Signal noise in the range of 50 to 100 RLU/second To each well is added 90 uL of premix. Read the chemiluminescence several times. Add 10 uL of enzyme or buffer to each well. Read chemiluminescence over several hours. Add 10 uL of enzyme or buffer to each well to give the indicated amounts of enzyme (buffer) in a 100 uL reaction. Buffer=10.0 mM $NaHCO_3$, 1% BSA. The buffer was also the diluent for the serial dilutions of the enzyme.

Each well contained 90 uL of solution comprised of 100 mM in $NaPO_4$. (pH=8.2), 100 mM NaCl, 50 mM MgCl2, 0.1 mM ZnCl2, 20% (v/v) DMF; 2.0% (v/v) Triton X-100; 211 uM Acl, and 1.00 mg/mL BCIP. The enzyme was added in the following amounts (in attomoles): (1) 806,000, (2) 80,600, (3) 8,060, (4) 806, (5) 80.60 (6) 8.06, (7) 0.806, and (8) 0.0806. Data shown are averages of two wells for the glucose oxidase samples and of eight wells for the blank.

4. Screening Reactions of 9-Acridinecarbonyl Chloride with Leaving Group Compounds

A. Phosphate Buffer, pH 8.2

Figure 7:
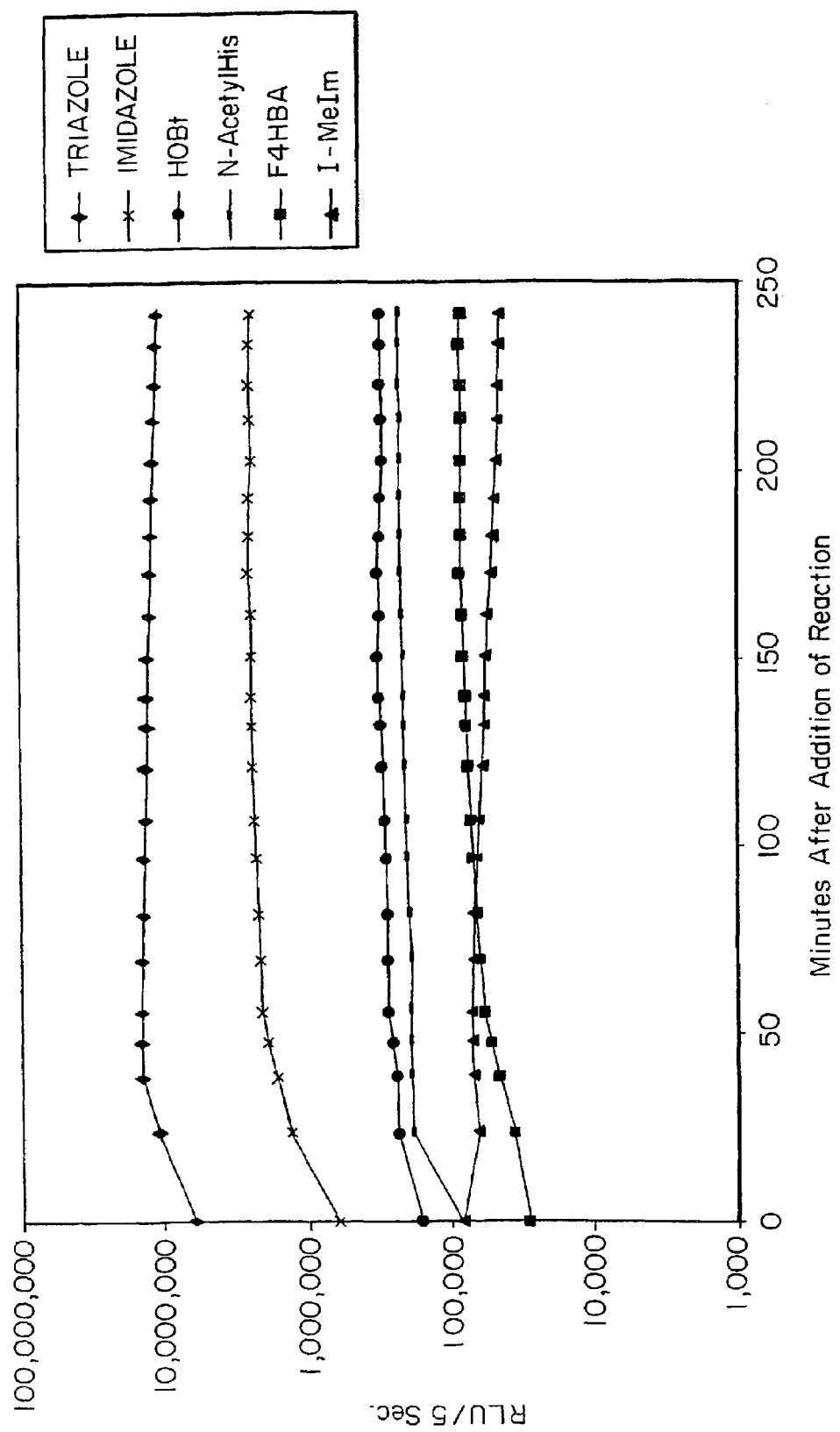
FIGS. 7-10 show the results of screening different reaction mixtures for chemiluminescence using different pH systems.

Reactions of 9-acridinecarbonyl chloride with several potential leaving group compounds were set up. Briefly, a solution of the hydrochloride salt of 9-acridinecarbonyl chloride (one to five micromoles) in acetonitrile was added separately to solutions of the compounds (at least 18 micromoles) to be tested. The solid compounds were in acetonitrile, N,N-dimethylformamide, or a mixture of these two solvents. Pyridine was added to most of these reactions to neutralize the acid from the carbonyl chloride and to insure that the tested compound was present in the nucleophilic, unprotonated form. The reactions were allowed to proceed at room temperature for at least 12 hours. To screen the products of these reactions for chemiluminescence near pH 8.2, polypropylene tubes with the equivalent of 50 uL of 100 mM sodium phosphate, pH 8.2, 40 uL of $H_2O$ and 5 uL of 800 mM $H_2O_2$ were prepared. At zero time 5 uL of each reaction was added to one of these tubes and the chemiluminesence was measured several times over several hours in a Magic Lite Analyzer II luminometer. Two types of kinetics were observed: plateau and decay. In FIG. 7 examples of plateau kinetics are shown and in FIG. 8 examples of decay kinetics are shown. Abbreviations in the figure legends are for the compound reacted with 9-acridinecarbonyl chloride: TRIAZOLE is 1, 2, 4-triazole; HOBt is 1-hydroxybenzotriazole; N-AcetylHis is N-α acetyl-L-histidine; F4HBA is 2,3,5,6-tetrafluoro-4-hydroxybenzoic acid; 1-MeIm is 1-methylimidazole.

Figure 8:
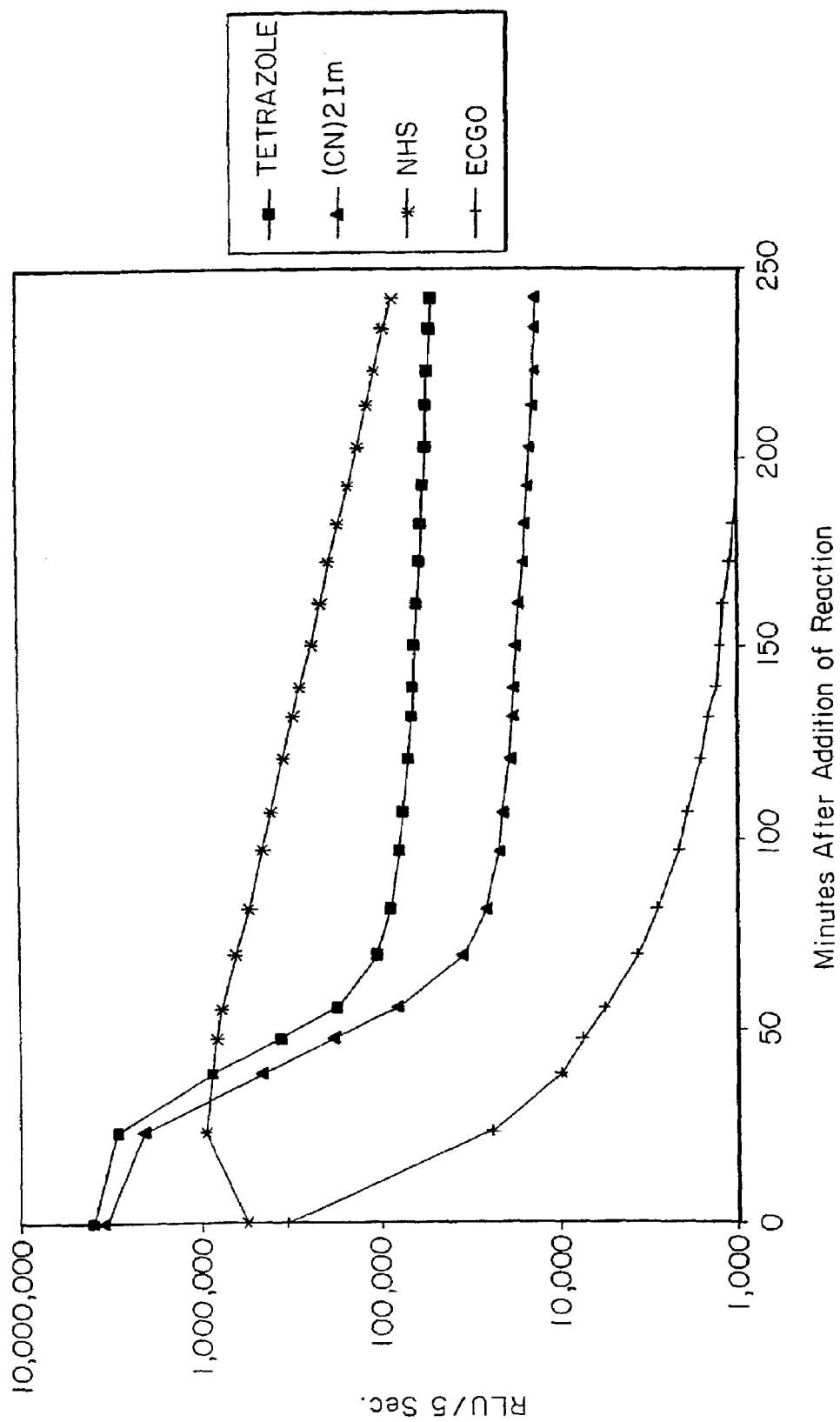

The abbreviations in FIG. 8 are: TETRAZOLE is 1H-tetrazole; (CN)2Im is 4,5-dicyanoimidazole; NHS is N-hydroxysuccinimide; and ECGO is ethyl cyanoglyoxylate-2-oxime. Note that even in the decay kinetics examples that the chemiluminescence is detectable for at least an hour. Of the reactions shown only the imidazole and the 1-methylimidazole reaction did not have pyridine. Note that for this screening procedure the unpurified crude reaction mixture was used.

B. Acetate Buffer, pH 5.5

Figure 9:
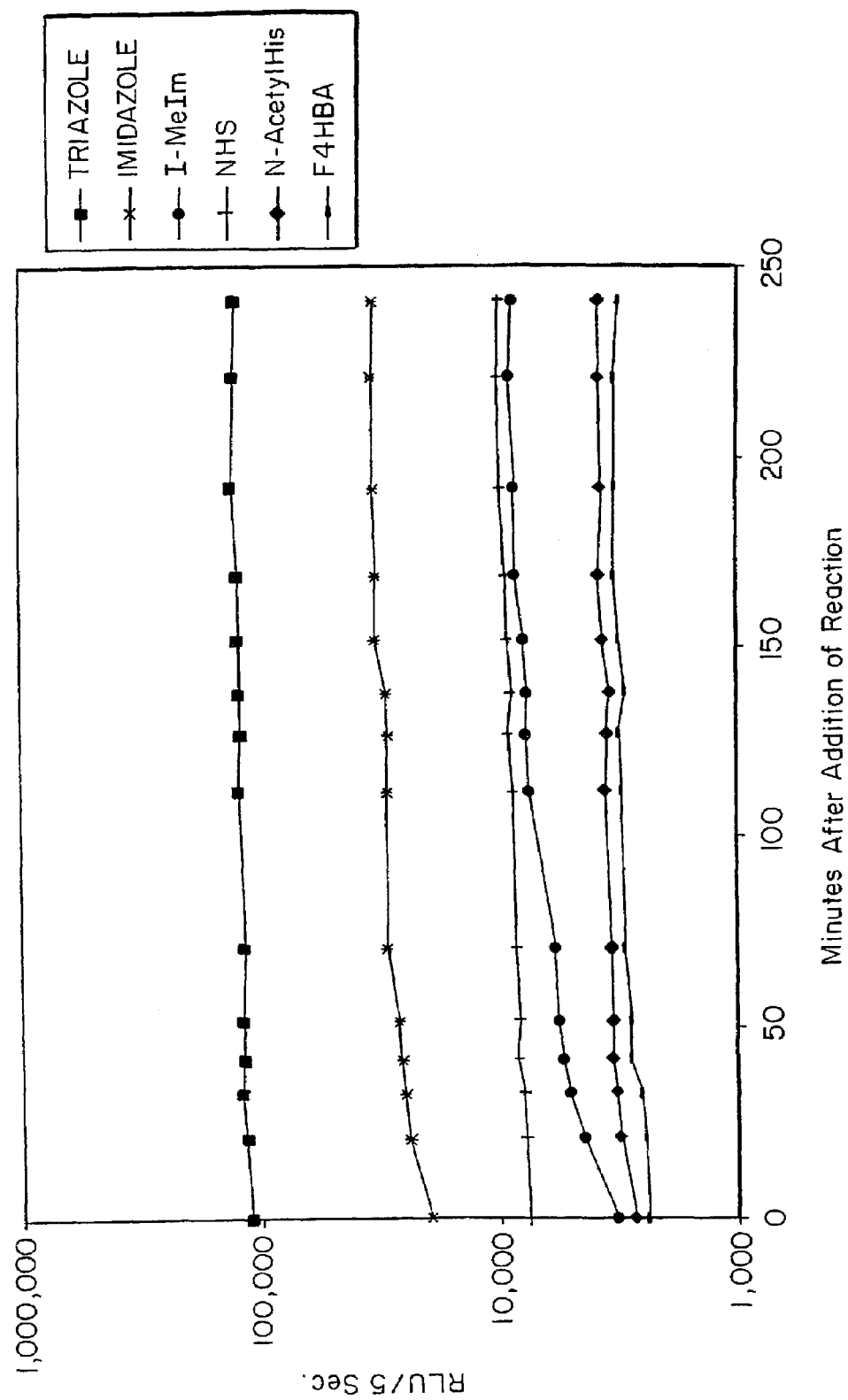
Figure 10:
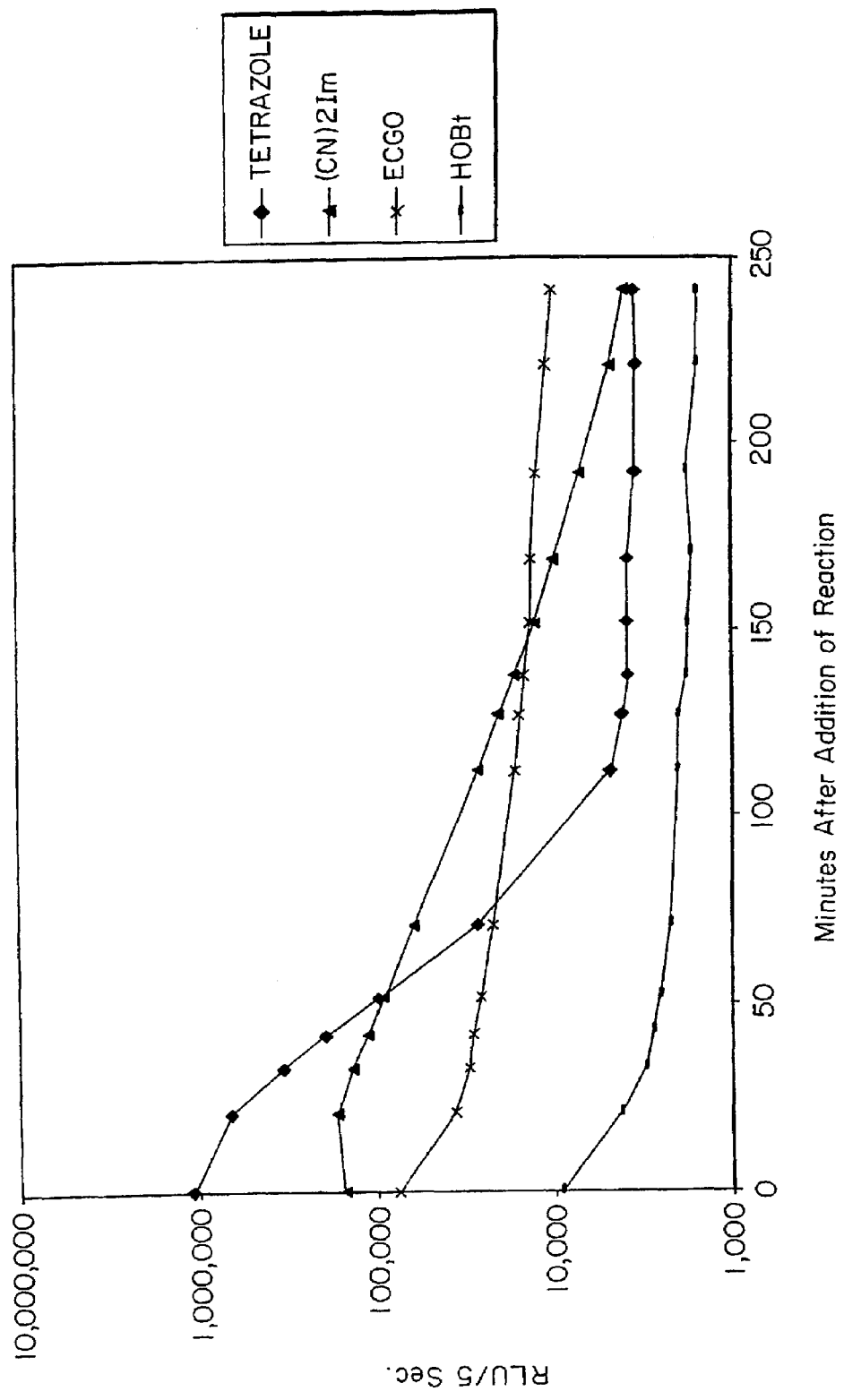

The screening procedure was repeated on the same reactions, substituting 100 mM sodium acetate buffer at pH 5.5 for the pH 8.2 sodium phosphate buffer. Again both plateau and decay kinetics were observed. FIG. 9 depicts plateau kinetics and FIG. 10 depicts decay kinetics.

The invention claimed is:

1. A method for detecting the presence of a peroxide compound or a free radical thereof comprising contacting an aqueous or mixed aqueous-organic solution of said peroxide compound or free radical thereof with a chemiluminescent agent and detecting the chemiluminesence generated by reaction of the chemiluminescent agent with the peroxide compound or free radical thereof to be detected, wherein said chemiluminescent agent comprises a chemiluminescent compound defined by the formula:

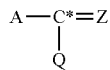

where $C^*$ is an $sp^2$ coordinated carbon atom;
A is defined by the formula

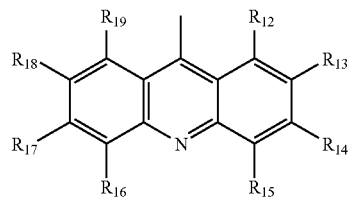

wherein $R_{12}$, $R_{13}$, $R_{14}$, $R_{15}$, $R_{16}$, $R_{17}$, $R_{18}$ and $R_{19}$ are independently selected from the group consisting of hydrogen, alkyl, alkoxy, aryl, alkylaryl, heteroaryl, heteroalkoxy, aldehyde, keto, amino, nitro, halo, sulfate, sulfonyl, carboxy, carboxyester, phosphate and phosphoester, each of which may be substituted or unsubstituted;

Z is O; and

Q is a suitable leaving group which yields a compound capable of exhibiting a chemiluminescent reaction in the presence of a peroxide or peroxide-like compound under aqueous or mixed aqueous-organic conditions, wherein the leaving group Q is an N-linked optionally substituted heterocyclic aryl moiety selected from the group consisting of imidazole, oxazole, thiazole, pyrazole, pyrimidine, purine, quinoline, isoquinoline, pyrrole, indole, pyridine, tetrazole, triazole, and carbazole, and detecting the chemiluminescence generated by reaction of said compound with said peroxide compound or free radical thereof to be detected.

2. A method of claim 1 wherein Q is N-linked imidazole or substituted imidazole.

3. A method of claim 1 wherein said peroxide compound or free radical thereof to be detected is hydrogen peroxide, an anion derived from hydrogen peroxide, a peracid or a hydroperoxide.

4. A method of claim 1 wherein said method comprises an assay for the presence or absence of an analyte which decreases the concentration of said peroxide compound or free radical thereof.

5. A method of claim 1 wherein said method is a competitive binding assay for the presence or absence of an analyte, and a binding partner for the analyte is conjugated to one of an enzyme, a substrate for such an enzyme, or said chemiluminescent compound.

6. A method of claim 5 wherein the analyte is a substrate for an enzymatic reaction which decreases the concentration of said peroxide compound or free radical thereof.

7. A method of claim 5 wherein the method is a competitive binding assay, for the presence or quantity of the analyte, in which sample analyte competes with a competitive binding reagent to bind to a binding partner, and the competitive binding reagent is conjugated to either the enzyme, a substrate for the enzyme, or said chemiluminescent compound, whereby increasing amounts of analyte result in a decrease in the amount of the competitive binding reagent conjugated to either the enzyme, a substrate for the enzyme, or said chemiluminescent compound, whereby increasing amounts of analyte result in a decrease in the amount of the competitive binding reagent conjugate, and increasing amounts of analyte thereby increasing the concentration of said peroxide compound or free radical thereof available to provide a chemiluminescent reaction.

8. A method of claim 1 wherein said method detects and/or measures by chemiluminescence enzymes that generate hydrogen peroxide or peroxide compounds, directly or indirectly.

9. A method of claim 1 wherein said method detects and/or measures by chemiluminescence enzymes that consume hydrogen peroxide or peroxide compounds.

10. A method of claim 1 wherein said method detects and/or measures antigens, protein ligands, nucleic acids, polysaccharides, and/or biopolymers, using an enzyme that generates or consumes, directly or indirectly, hydrogen peroxide or peroxide compounds.

11. A method of claim 1 wherein said peroxide compound comprises hydrogen peroxide which is the product of a reaction between an analyte, whose presence or absence is to be determined, and a reactant which reaction yields hydrogen peroxide.

12. A method of claim 1 wherein Q is N-linked pyridine or substituted pyridine.

13. A method of claim 1 wherein the leaving group is defined by the formula

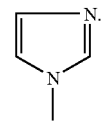

14. A method of claim 1 wherein the leaving group is defined by the formula

15. A method of claim 1 wherein the leaving group is defined by the formula

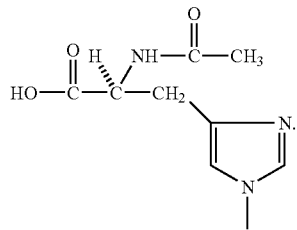

16. A method of claim 1 wherein the leaving group is defined by the formula

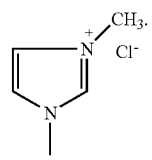

17. A method of claim 1 wherein the leaving group is defined by the formula

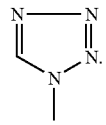

18. A method of claim 1 wherein the leaving group is defined by the formula

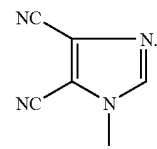

19. A method of claim 1 wherein Q is N-linked triazole or substituted triazole.

20. A method of claim 1 wherein Q is N-linked tetrazole.

* * * * *